US009751827B2

(12) United States Patent
Ogata et al.

(10) Patent No.: US 9,751,827 B2
(45) Date of Patent: Sep. 5, 2017

(54) METHOD FOR ALKYLATION OF AMINES

(71) Applicant: Takasago International Corporation, Tokyo (JP)

(72) Inventors: Osamu Ogata, Kanagawa (JP); Hideki Nara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 44 days.

(21) Appl. No.: 14/772,513

(22) PCT Filed: Jan. 21, 2014

(86) PCT No.: PCT/JP2014/000267
§ 371 (c)(1),
(2) Date: Sep. 3, 2015

(87) PCT Pub. No.: WO2014/136374
PCT Pub. Date: Sep. 12, 2014

(65) Prior Publication Data
US 2016/0009632 A1    Jan. 14, 2016

(30) Foreign Application Priority Data
Mar. 4, 2013 (JP) ................................ 2013-041760

(51) Int. Cl.
*C07C 209/02* (2006.01)
*B01J 31/24* (2006.01)
*C07D 213/74* (2006.01)
*C07D 295/023* (2006.01)
*B01J 31/20* (2006.01)
*C07D 213/72* (2006.01)

(52) U.S. Cl.
CPC ............. *C07C 209/02* (2013.01); *B01J 31/20* (2013.01); *B01J 31/24* (2013.01); *B01J 31/248* (2013.01); *C07D 213/72* (2013.01); *C07D 213/74* (2013.01); *C07D 295/023* (2013.01); *B01J 2231/44* (2013.01); *B01J 2531/821* (2013.01); *C07C 2103/74* (2013.01)

(58) Field of Classification Search
CPC .......... B01J 31/20; B01J 31/24; B01J 31/248; C07C 209/02; C07C 2103/74; C07D 211/48; C07D 213/72
USPC ........................ 546/184, 304; 556/8; 564/415
See application file for complete search history.

(56) References Cited

U.S. PATENT DOCUMENTS 8,471,048 B2 * 6/2013 Kuriyama ............... C07B 53/00
556/8
9,000,212 B2 * 4/2015 Touge ..................... C07C 67/40
546/137
2011/0237814 A1 9/2011 Kuriyama et al.
2013/0172619 A1 7/2013 Ogata et al.

FOREIGN PATENT DOCUMENTS

| CN | 102177170 A | 9/2011 |
| CN | 103237779 A | 8/2013 |
| EP | 2492275 A1 | 8/2012 |
| EP | 2619162 A1 | 7/2013 |
| JP | 2012-67021 A | 4/2012 |
| WO | WO-2011/048727 A1 | 4/2011 |
| WO | WO-2012/039098 A1 | 3/2012 |
| WO | WO-2012/144650 A1 | 10/2012 |

OTHER PUBLICATIONS

Bahn et al. "Ruthenium catal . . . " Adv. Synth. Catal. 350, 2099-2103 (2008).*
Bertoli et al. "Osmium and ruthenium . . . " Organometallics, 30, 3479-3482 (2011).*
Cade et al. "Five coordina . . . " Organometallics, 29, 4012-4017 (2010).*
Ho "Fieser's Reagent . . . " v.25, p. 61-66 (2010).*
Hamid et al. "Ruthenium catalyzed . . . " J. Am. Chem. Soc., 131, 1766-1774 (2009).*
Lorentz "Iridium and Ruthenium . . . " thesis, p. 1-189 (2012).*
English translation of International Preliminary Report on Patentability issued in corresponding International Application Ser. No. PCT/JP2014/000267, filed Jan. 21, 2014, 9 pages.
Organometallics, 2011, vol. 30, No. 13, p. 3479-3482.
Polyhedron, Mar. 22, 2013, vol. 52, p. 1024-1029.
International Search Report and Written Opinion for corresponding International Application Ser. No. PCT/JP2014/000267, Mar. 4, 2014, 10 pages.
Tetrahedron Letters (2003), 44 (13), 2687-2690.
Synlett (2005), (4), 560-571.
Advanced Synthesis & Catalysis (2008), 350 (5), 749-758.
RSC Advances (2012), 2 (23), 8645-8652.
Advanced Synthesis & Catalysis (2007), 349 (10), 1555-1575.
Chemistry Letters (1988), 17 (3), 449-452.
European Journal of Inorganic Chemistry (2004), (3), 524-529.

* cited by examiner

*Primary Examiner* — Heidi Reese
(74) *Attorney, Agent, or Firm* — Mintz Levin Cohn Ferris Glovsky and Popeo, P.C.; Peter F. Corless

(57) ABSTRACT

The present invention provides a simple, efficient, and industrially advantageous method for the alkylation of amines. The present invention relates to a production method for N-alkylamines whereby an amine is reacted with an alcohol in the presence of a ruthenium complex represented by general formula (1): RuXY(CO)(L) (wherein X and Y can be the same or different and represent a monovalent anionic ligand, and L represents a tridentate aminodiphosphine ligand).

15 Claims, No Drawings

METHOD FOR ALKYLATION OF AMINES

CROSS-REFERENCE TO RELATED APPLICATIONS

The present application is the U.S. national stage pursuant to 35 U.S.C. §371, of Japanese international application Ser. No. PCT/JP2014/000267, filed Jan. 21, 2014 and published on Sep. 12, 2014 as publication WO 2014/136374 A1, which claims priority to Japanese patent application No. 2013-041760, filed Mar. 4, 2013. The entire teachings of this application are incorporated herein by reference.

TECHNICAL FIELD

The present invention relates to a method for catalytically alkylating amines by using alcohols.

BACKGROUND ART

A reaction for the N-alkylation of amines is an industrially important reaction. As this reaction, techniques using methyl iodide, dimethyl sulfate and the like as alkylating agents are known, but many of the alkylating agents are mutagenic substances, and thus safer techniques are desired. One of the safer techniques includes alkylation using a transition metal as a catalyst wherein an alcohol is used as a carbon source.

Examples of the catalyst include heterogeneous catalysts and homogeneous catalysts comprising platinum or chromium. Since heterogeneous catalysts generally require a high temperature and a high pressure and thus have problems in safeness, homogeneous catalysts are more advantageous in industry.

As homogeneous catalysts, complexes comprising metals such as iridium, rhodium and ruthenium are known.

As examples using an iridium complex, monoalkylation of an amine using an alcohol catalyzed by an arene-type complex described in Non Patent Documents 1 and 2, and alkylation of a heteroamine with a complex bearing a P,N ligand described in Non Patent Document 3 are known. Furthermore, as an example using methanol as a carbon source, the example described in Non Patent Document 4 is known.

Regarding ruthenium, the reaction for dimethylating an amine using methanol as a carbon source described in Non Patent Document 5 is known. Furthermore, Non Patent Document 6 describes a reaction for monomethylating an aniline using methanol as a carbon source and using ruthenium trichloride and a trialkoxyphosphine as catalysts.

Ruthenium is more advantageous in industry than iridium and rhodium since it is an inexpensive metal. Ruthenium complexes that catalyze an N-methylation reaction using an alcohol are reported in Non Patent Documents 5, 6, 7 and the like, but any example of a report in which a Pincer type ruthenium complex having a tridentate ligand is used is not known. Furthermore, reactions using the ruthenium complexes described in said Non Patent Documents require a much amount of catalyst, there are problems in costs and the like for industrialization.

Furthermore, as a catalyst for reducing a carbonyl group in a ketone, an ester or the like, a ruthenium complex having a tridentate ligand and a carbonyl ligand, wherein the tridentate ligand comprises two phosphino groups and a —NH— group, has been already reported (see Patent Document 1). However, said documents are silent about a catalytic ability in alkylation of an amines.

CITATION LISTS

Patent Documents

Patent Document 1: WO 2011/048727 A1

Non Patent Documents

Non Patent Document 1: Tetrahedron Letters (2003), 44 (13), 2687-2690
Non Patent Document 2: Synlett (2005), (4), 560-571
Non Patent Document 3: Advanced Synthesis & Catalysis (2008), 350 (5), 749-758
Non Patent Document 4: RSC Advances (2012), 2 (23), 8645-8652
Non Patent Document 5: Advanced Synthesis & Catalysis (2007), 349 (10), 1555-1575
Non Patent Document 6: Chemistry Letters (1988), 17 (3), 449-452
Non Patent Document 7: European Journal of Inorganic Chemistry (2004), (3), 524-529

SUMMARY OF THE INVENTION

Problems to be Solved by the Invention

The object of the present invention is to provide a method for efficiently alkylating amines by using a ruthenium complex, which is easily produced and handled, and can be obtained at a relatively low cost.

Means for Solving the Problems

In view of the above-mentioned circumstance, the present inventors conducted intensive studies, and consequently found that amines can be efficiently alkylated by using a ruthenium complex, as a catalyst for alkylation reaction, having a tridentate ligand comprising two phosphino groups and an —NH— group and a carbonyl ligand, and completed the present invention.

The present invention relates to the following [1] to [9].

[1] A method for producing an N-alkylamine, comprising reacting an amine with an alcohol in the presence of a ruthenium complex represented by the following general formula (1):

$$RuXY(CO)(L) \qquad (1)$$

wherein, in the general formula (1), X and Y may be the same or different from each other, and each represents a monovalent anionic ligand, and L represents a tridentate aminodiphosphine ligand represented by the following general formula (2):

[Chemical Formula 1]

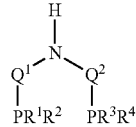

(2)

wherein, in the general formula (2),
$R^1$, $R^2$, $R^3$ and $R^4$ may be the same or different from one another, and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group or a substituted amino group, wherein $R^1$ and $R^2$ or $R^3$ and $R^4$ may bind to each other to form a ring together with the adjacent phosphorus atom, and said alkyl group, cycloalkyl group, aryl group, aralkyl group, alkyloxy group, cycloalkyloxy group, aryloxy group, aralkyloxy group, heterocyclic group and substituted amino group may have substituent(s); and $Q^1$ and $Q^2$ may be the same or different from each other, and each represents an optionally substituted divalent alkylene group, an optionally substituted divalent cycloalkylene group or an optionally substituted divalent aralkylene group.

[2] The production method according to [1], wherein L is a tridentate aminodiphosphine ligand represented by the following general formula (3):

[Chemical Formula 2]

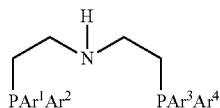

(3)

wherein, in the general formula (3), $Ar^1$, $Ar^2$, $Ar^3$ and $Ar^4$ may be the same or different from one another, and each represents an optionally substituted aryl group or an optionally substituted aromatic heterocyclic group.

[3] The production method according to [1] or [2], wherein the N-alkylamine has the following general formula (4):

 (4)

wherein in the general formula (4), $R^4$ represents an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s); and R represents an optionally substituted hydrocarbon group, an optionally substituted aryl group or an optionally substituted heterocyclic group, wherein the amine has the following general formula (5):

 (5)

wherein, in the general formula (5), $R^4$ represents the same group as in the definition in the general formula (4), and the alcohol has the following general formula (6):

 (6)

wherein, in the general formula (6), R represents the same group as in the definition in the general formula (4).

[4] The production method according to [1] or [2], wherein the N-alkylamine has the following general formula (7):

[Chemical Formula 3]

(7)

wherein, in the general formula (7), $R^{B1}$ represents a hydrogen atom, an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s);

$R^{B2}$ represents an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s);

wherein $R^{B1}$ and $R^{B2}$ may bind to each other to form a ring together with the adjacent nitrogen atom; and R represents an optionally substituted hydrocarbon group, an optionally substituted aryl group or an optionally substituted heterocyclic group, wherein the amine has the following general formula (8):

[Chemical Formula 4]

(8)

wherein, in the general formula (8), $R^{B1}$ and $R^{B2}$ each represents the same group as the definition in the general formula (7), and the alcohol has the following general formula (6):

 (6)

wherein, in the general formula (6), R represents the same group as mentioned above.

[5] The production method according to [1] or [2], wherein the N-alkylamine has the following general formula (9):

[Chemical Formula 5]

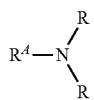

(9)

wherein, in the general formula (9), $R^4$ represents an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s); and R represents an optionally substituted hydrocarbon group, an optionally substituted aryl group or an optionally substituted heterocyclic group, wherein the amine has the following general formula (5):

wherein, in the general formula (5), $R^A$ represents the same group as mentioned above, and the alcohol has the following general formula (6):

wherein, in the general formula (6), R represents the same group as mentioned above.

[6] The method according to any one of [1] to [5], wherein the alcohol is a primary or secondary alcohol.

[7] The method according to any one of [1] to [6], wherein the alcohol is methanol or ethanol.

[8] The method according to any one of [1] to [7], wherein the reaction of the amine and the alcohol is conducted in the presence of a basic substance.

[9] The method according to [8], wherein the basic substance is a metal alkoxide.

Effects of the Invention

According to the present invention, alkylated amines can be produced directly from alcohols and amines in the presence of a suitable amount of ruthenium catalyst under reaction conditions that are suitable for industrial use, wherein the alcohols are used as alkylating agents.

The ruthenium catalysts used in the method of the present invention are easily prepared and also have high stability and are easily handled, and thus are suitable for industrial use. Therefore, substitution reaction of amines can be conducted in a convenient and efficient manner in an industrial method by the use of the ruthenium catalysts.

DESCRIPTION OF EMBODIMENTS

The ruthenium carbonyl complex represented by the following general formula (1) used for the present invention will be described.

The tridentate aminodiphosphine ligand represented by L in the general formula (1) includes a tridentate aminodiphosphine ligand comprising two phosphino groups and a —NH— group. A specific tridentate aminodiphosphine ligand includes a tridentate aminodiphosphine ligand represented by the following general formula (2).

[Chemical Formula 6]

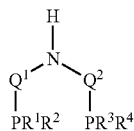

$R^1$, $R^2$, $R^3$ and $R^4$ in the general formula (2) will be described.

$R^1$, $R^2$, $R^3$ and $R^4$ in the general formula (2) may be the same or different from one another, and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group or a substituted amino group, wherein $R^1$ and $R^2$ or $R^3$ and $R^4$ may bind to each other to form a ring together with the adjacent phosphorus atom. Furthermore, these alkyl group, cycloalkyl group, aryl group, aralkyl group, alkyloxy group, cycloalkyloxy group, aryloxy group, aralkyloxy group, heterocyclic group and substituted amino group may have substituent(s).

As the alkyl group, linear or branched alkyl group having 1 to 50 carbon atoms, preferably 1 to 20 carbon atoms, more preferably 1 to 10 carbon atoms is exemplified. Examples of the alkyl group include a methyl group, an ethyl group, an n-propyl group, an isopropyl group, an n-butyl group, an isobutyl group, an s-butyl group, a tert-butyl group, an n-pentyl group, an n-hexyl group, an n-octyl group, and the like.

As the cycloalkyl group, a monocyclic, polycyclic, condensed cyclic or bridged cycloalkyl group having 3 to 30 carbon atoms, preferably 3 to 20 carbon atoms, more preferably 3 to 10 carbon atoms is exemplified. Examples of the cycloalkyl group include a cyclopropyl group, a cyclopentyl group, a cyclohexyl group, a cyclooctyl group, a bicyclo[1.1.0]butyl group, a tricyclo[2.2.1.0]heptyl group, a bicyclo[3.2.1]octyl group, a bicyclo[2.2.2.]octyl group, an adamantyl group (a tricyclo[3.3.1.1]decanyl group), a bicyclo[4.3.2] undecanyl group, a tricyclo[5.3.1.1]dodecanyl group, and the like.

As the aryl group, a monocyclic, polycyclic or condensed cyclic aryl group having 6 to 36 carbon atoms, preferably 6 to 18 carbon atoms, more preferably 6 to 14 carbon atoms is exemplified. Specific examples of the aryl group include a phenyl group, a naphthyl group, an anthryl group, a phenanthryl group, a biphenyl group, and the like.

As the aralkyl group, a group in which at least one hydrogen atom(s) of the above-mentioned alkyl groups has/have been substituted with the above-mentioned aryl group(s) is exemplified. Furthermore, an aralkyl group having 7 to 37 carbon atoms, preferably 7 to 20 carbon atoms, more preferably 7 to 15 carbon atoms is exemplified. Specific examples of the aralkyl group include a benzyl group, a 1-phenylethyl group, a 2-phenylethyl group, a 1-phenylpropyl group, a 3-naphthylpropyl group, and the like.

As the alkyloxy group, an alkyloxy group comprising linear or branched alkyl group having 1 to 20 carbon atoms, preferably 1 to 15 carbon atoms, more preferably 1 to 10 carbon atoms is exemplified. Examples of the alkyloxy group include a methoxy group, an ethoxy group, an n-propoxy group, an isopropoxy group, an n-butoxy group, an isobutoxy group, an s-butoxy group, a tert-butoxy group, an n-pentyloxy group, and the like.

As the cycloalkyloxy group, a cycloalkyloxy group comprising a polycyclic or condensed cyclic cycloalkyl group having 3 to 20 carbon atoms, preferably 3 to 15 carbon atoms, more preferably 3 to 10 carbon atoms is exemplified. Examples of the cycloalkyloxy group include a cyclopropyloxy group, a cyclopentyloxy group, a cyclohexyloxy group, and the like.

As the aryloxy group, an aryloxy group comprising a monocyclic, polycyclic or condensed cyclic aryl group having 6 to 36 carbon atoms, preferably 6 to 18 carbon atoms, more preferably 6 to 14 carbon atoms is exemplified. Specific examples of the aryloxy group include a phenoxy group, a tolyloxy group, a xylyloxy group, a naphthyloxy group, and the like.

As the aralkyloxy group, a group in which at least one hydrogen atom(s) of the alkyl groups or cycloalkyl groups of the above-mentioned alkyloxy groups has/have been substituted with the above-mentioned aryl group(s) is exemplified. Preferable examples of the aralkyloxy group include an aralkyloxy group having 7 to 15 carbon atoms. Specific examples of the aralkyloxy group include a benzyloxy group, a 1-phenylethoxy group, a 2-phenylethoxy group, a 1-phenylpropoxy group, a 2-phenylpropoxy group, a 3-phenylpropoxy group, a 4-phenylbutoxy group, a 1-naphthylmethoxy group, a 2-naphthylmethoxy group, and the like.

As the heterocyclic group, an aliphatic heterocyclic group and an aromatic heterocyclic group are exemplified. The aliphatic heterocyclic groups include, for example, 3- to 8-membered, preferably 4- to 6-membered monocyclic aliphatic heterocyclic groups and polycyclic or condensed ring aliphatic heterocyclic groups each having 2 to 14 carbon atoms and containing at least one, preferably 1 to 3 heteroatom(s) such as a nitrogen atom, an oxygen atom and/or a sulfur atom as heteroatom(s). Specific examples of the aliphatic heterocyclic groups include an azetidyl group, an azetidino group, a pyrrolidyl group, a pyrrolidino group, a piperidinyl group, a piperidino group, a piperazinyl group, a piperazino group, a morpholinyl group, a morpholino group, a tetrahydrofuryl group, a tetrahydropyranyl group, a tetrahydrothiophenyl group, and the like.

Examples of the aromatic heterocyclic groups include 5- or 6-membered monocyclic heteroaryl groups, polycyclic or condensed cyclic heteroaryl groups, each having 2 to 15 carbon atoms and containing at least one, preferably 1 to 3 heteroatom(s) such as a nitrogen atom, oxygen atom and/or a sulfur atom as heteroatom(s). Specific examples of the aromatic heterocyclic group include a furyl group, a thienyl group, a pyridyl group, a pyrimidyl group, a pyrazyl group, a pyridazyl group, a pyrazolyl group, an imidazolyl group, an oxazolyl group, a thiazolyl group, a benzofuryl group, a benzothienyl group, a quinolyl group, an isoquinolyl group, a quinoxalyl group, a phthalazyl group, a quinazolyl group, a naphtylidyl group, a cinnolyl group, a benzimidazolyl group, a benzoxazolyl group, a benzothiazolyl group, an acridyl group, an acridinyl group, and the like.

As the substituted amino groups, an amino group in which the two hydrogen atoms of the amino group have been substituted with the same or different groups, wherein the substituents include alkyl groups, cycloalkyl groups, aryl groups, aralkyl groups, and/or heterocyclic groups which are all mentioned above is exemplified. Specific examples of the substituted amino groups include dialkylamino groups such as an N,N-diethylamino group and an N,N-diisopropylamino group; dicycloalkylamino groups such as an N,N-dicyclohexylamino group; diarylamino groups such as an N,N-diphenylamino group and an N-naphthyl-N-phenylamino group; diaralkylamino groups such as an N,N-dibenzylamino group, and the like. Furthermore, the alkyl groups, cycloalkyl groups, aryl groups, aralkyl groups and heterocyclic groups of the substituted amino groups may further have substituent(s).

The substituents that may be carried by said alkyl groups, cycloalkyl groups, aryl groups, aralkyl groups, alkyloxy groups, cycloalkyloxy groups, aryloxy groups, aralkyloxy groups, heterocyclic groups, and by the alkyl groups, cycloalkyl groups, aryl groups, aralkyl groups and heterocyclic groups as the substituents of the substituted amino groups include the above-mentioned alkyl groups, the above-mentioned cycloalkyl groups, the above-mentioned aryl group, the above-mentioned aralkyl groups, the above-mentioned alkyloxy groups, the above-mentioned cycloalkyloxy groups, the above-mentioned aryloxy groups, the above-mentioned aralkyloxy groups, the above-mentioned heterocyclic groups, the above-mentioned substituted amino groups, halogen atoms, silyl groups and optionally protected hydroxyl groups, and the like.

The halogen atoms as the substituents for $R^1$, $R^2$, $R^3$ and $R^4$ include a fluorine atom, a chlorine atom, a bromine atom and an iodine atom.

The silyl groups as the substituents for $R^1$, $R^2$, $R^3$ and $R^4$ include a silyl group in which three hydrogen atoms in the silyl group have been substituted with the above-mentioned alkyl groups, the above-mentioned cycloalkyl groups, the above-mentioned aryl groups, the above-mentioned aralkyl groups, and the like. Specific examples of the substituted silyl group include a trimethylsilyl group, a triethylsilyl group, a t-butyldimethylsilyl group, a t-butyldiphenylsilyl group, a triphenylsilyl group, and the like.

The optionally protected hydroxyl groups as the substituents for $R^1$, $R^2$, $R^3$ and $R^4$ include unprotected hydroxyl groups and hydroxyl groups that may be protected with general protective groups for hydroxyl groups used in the peptide synthesis described in Reference Document 1 (Protective Groups in Organic Synthesis Second Edition, JOHN WILEY & SONS, INC. 1991), and the like, such as silyl groups including a trimethylsilyl group, a tert-butyldimethylsilyl group and a tert-butyldiphenylsilyl group, and the like, a benzyl group and a methoxymethyl group.

Said $R^1$ and $R^2$ or $R^3$ and $R^4$ may bind to each other to form a ring together with the adjacent phosphorus atom. Preferable bound groups in the case where $R^1$ and $R^2$ or $R^3$ and $R^4$ form a ring include linear or branched divalent alkylene groups such as linear or branched divalent alkylene groups having 2 to 20 carbon atoms, preferably 4 to 10 carbon atoms, more preferably 4 to 6 carbon atoms; and linear or branched divalent alkenylene groups having 4 to 20 carbon atoms, preferably 4 to 10 carbon atoms, more preferably 4 to 6 carbon atoms. Said divalent groups may have substituent(s) mentioned above.

$Q^1$ and $Q^2$ in the general formula (2) will be described.

$Q^1$ and $Q^2$ in the general formula (2) may be the same or different from each other, and each represents an optionally substituted divalent alkylene group, an optionally substituted divalent cycloalkylene group or an optionally substituted divalent aralkylene group.

The divalent alkylene group includes linear or branched divalent alkyl chains having 1 to 20 carbon atoms, preferably 1 to 10 carbon atoms, more preferably 1 to 6 carbon atoms. Specific examples of the divalent alkyl group include a methylene group, an ethylene group, a trimethylene group, a tetramethylene group, a pentamethylene group, and the like.

As the divalent cycloalkylene group, a divalent cycloalkylene group comprising a monocyclic, polycyclic or condensed cyclic cycloalkyl group having 3 to 15 carbon atoms, preferably 3 to 10 carbon atoms, more preferably 3 to 6 carbon atoms is exemplified. Examples of the divalent cycloalkylene group include a cyclopropylene group, a cyclobutylene group, a cyclopentylene group, a cyclohexylene group, and the like.

As the divalent aralkylene group, a divalent aralkylene group having 7 to 11 carbon atoms in which one hydrogen atom has been removed from the aryl group of the aralkyl group such as a benzyl group, a phenethyl group, and the like is exemplified. A benzylene group (-Ph-CH$_2$—), a 2-phenylethylene group (-Ph-CH$_2$CH$_2$—), a 1-naphthylmethylene group (—Np—CH$_2$—), a 2-naphthylmethylene group (—Np—CH$_2$—), and the like (wherein, in the formulas, -Ph- represents a phenylene group, and —Np— represents a naphthylene group) are exemplified.

The substituents that may be carried by said divalent alkylene groups, divalent cycloalkylene groups or divalent aralkylene groups include the alkyl groups, cycloalkyl groups, aryl groups, aralkyl groups, alkyloxy groups, cycloalkyloxy groups, aryloxy groups, aralkyloxy groups and heterocyclic groups, and the halogen atoms, silyl groups, substituted amino groups and optionally protected hydroxyl groups as those mentioned in the definition of $R^1$, $R^2$, $R^3$ and $R^4$ in the above-mentioned general formula (2), and the like.

Next, the monovalent anionic ligand represented by X or Y in the general formula (1) will be described.

As the monovalent anionic ligand, a hydride, an alkyloxy group, a cycloalkyloxy group, an aryloxy group, an aralkyloxy group, a hydroxy group, an acyloxy group, a sulfonyloxy groups, a halide ion, AlH$_4^-$, AlH$_2$(OCH$_2$CH$_2$OCH$_3$)$_2^-$, BH$_4^-$, BH$_3$CN$^-$, BH(Et)$_3^-$ and BH(sec-Bu)$_3^-$, and the like are exemplified. In this specification, the hydride is also simply referred to as hydrogen, and the halide ion is also simply referred to as halogen.

The alkyloxy groups, cycloalkyloxy groups, aryloxy groups and aralkyloxy groups include the groups described in the above-mentioned general formula (2).

The acyloxy groups include those represented by (R$^a$CO$_2$). As R$^a$ in the acyloxy group R$^a$CO$_2$, a hydrogen atom, an alkyl group, a cycloalkyl group, an aryl group and an aralkyl group are exemplified. Examples of the alkyl group, cycloalkyl group, aryl group and aralkyl group include the alkyl groups, cycloalkyl groups, aryl groups and aralkyl groups as those mentioned in the definition of $R^1$, $R^2$, $R^3$ and $R^4$ in the above-mentioned general formula (2). Said alkyl group, cycloalkyl group, aryl group and aralkyl group as the R$^a$ may further be substituted with the alkyl groups, cycloalkyl groups, aryl groups, aralkyl groups, alkyloxy groups, cycloalkyloxy groups, aralkyloxy groups, aryloxy groups and heterocyclic groups, and the halogen atoms, silyl groups, optionally protected hydroxyl groups and optionally protected amino groups, and the like as those mentioned in the definition of $R^1$, $R^2$, $R^3$ and $R^4$ in the above-mentioned general formula (2).

The optionally protected amino group as the substituents for R$^a$ includes an unprotected amino group; a mono- or dialkylamino group such as an N-methylamino group, an N,N-dimethylamino group, an N,N-diethylamino group, an N,N-diisopropylamino group and an N-cyclohexylamino group; a mono- or diarylamino groups such as an N-phenylamino group, an N,N-diphenylamino group, an N-naphthylamino group and an N-naphthyl-N-phenylamino group; a mono- or diaralkylamino group such as an N-benzylamino group and an N,N-dibenzylamino group; an acylamino group such as a formylamino group, an acetylamino group, a propionylamino group, a pivaloylamino group, a pentanoylamino group, a hexanoylamino group and a benzoylamino group; an alkoxycarbonylamino group such as a methoxycarbonylamino group, an ethoxycarbonylamino group, an n-propoxycarbonylamino group, an n-butoxycarbonylamino group, a tert-butoxycarbonylamino group, a pentyloxycarbonylamino group and a hexyloxycarbonylamino group; an aryloxycarbonylamino group such as a phenyloxycarbonylamino group; an aralkyloxycarbonylamino group such as a benzyloxycarbonylamino group, and the like. Examples of the optionally protected amino groups include amino groups that are protected by general protective groups for amino groups used in the peptide synthesis described in the above-mentioned Reference Document 1, and the like.

Examples of R$^a$ include a methyl group, an ethyl group, a propyl group, a tert-butyl group, a trifluoromethyl group, a phenyl group, a pentafluorophenyl group and the like.

As the sulfonyloxy group, a sulfonyloxy group represented by (R$^S$SO$_3$) is exemplified. Examples of R$^S$ in the sulfonyloxy group R$^S$SO$_3$ include those defined as R$^a$ in the acyloxy groups, and the like.

The halide ion includes a fluoride ion, a chloride ion, a bromide ion and an iodide ion. Preferably, a chloride ion and a bromide ion are exemplified. Further preferably, a chloride ion is exemplified.

As the preferable monovalent anionic ligand, BH$_4^-$, a hydride and a chloride ion are exemplified.

A preferable tridentate aminophosphine ligand includes a tridentate aminophosphine ligand represented by the following general formula (10).

[Chemical Formula 7]

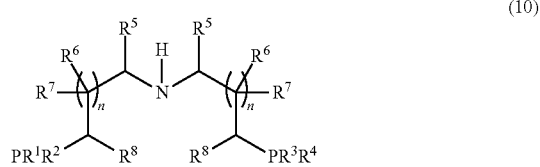

(10)

In the general formula (10), an alkyl group, a cycloalkyl group, an aryl group and an aralkyl group represented by R$^5$, R$^6$, R$^7$ and R$^8$ include the alkyl group, cycloalkyl group, aryl group and aralkyl group which are all mentioned in the definition of R$^1$, R$^2$, R$^3$ and R$^4$ in the above-mentioned general formula (2). Furthermore, the substituents that may be carried by said alkyl group, cycloalkyl group, aryl group and aralkyl group of the R$^5$, R$^6$, R$^7$ and R$^8$ include the alkyl groups, cycloalkyl groups, aryl groups, aralkyl groups, alkyloxy groups, cycloalkyloxy groups, aralkyloxy groups, aryloxy groups and heterocyclic groups, and the halogen atoms, silyl groups, substituted amino groups and optionally protected hydroxyl groups, and the like as those mentioned in the definition of R$^1$, R$^2$, R$^3$ and R$^4$ in the above-mentioned general formula (2).

In these R$^5$, R$^6$, R$^7$ and R$^8$, two R$^5$s, R$^5$ and R$^6$ or R$^7$ or R$^8$, R$^6$ and R$^7$ or R$^8$ may bind to each other to form a ring together with the adjacent carbon atom. The preferable groups in the case where a ring is formed include linear or branched divalent alkylene groups having 2 to 20 carbon atoms, preferably 4 to 10 carbon atoms, more preferably 4 to 6 carbon atoms; and linear or branched divalent alkenylene groups having 4 to 20 carbon atoms, preferably 4 to 10 carbon atoms, more preferably 4 to 6 carbon atoms.

These divalent groups may have substituent(s) as those mentioned in the definition of $R^1$, $R^2$, $R^3$ and $R^4$. Furthermore, the alkylene chains or alkenylene chains may contain one or two or more phenylene group(s).

A more preferable tridentate amino diphosphine ligand includes a tridentate aminodiphosphine ligand represented by the following general formula (3).

[Chemical Formula 8]

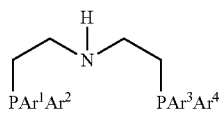

(3)

In the general formula (3), $Ar^1$, $Ar^2$, $Ar^3$ and $Ar^4$ may be the same or different from one another and each represents an aryl group or an aromatic heterocyclic group. Furthermore, said aryl group and aromatic heterocyclic group may have substituent(s).

Examples of the aryl group and aromatic heterocyclic group in the general formula (3) include the aryl groups as those mentioned in the definition of $R^1$, $R^2$, $R^3$ and $R^4$ in the general formula (2), and the aromatic heterocycles as those mentioned in the heterocycles, and the like. The substituents that may be carried by said aryl group and aromatic heterocyclic group as the $Ar^1$, $Ar^2$, $Ar^3$ and $Ar^4$ include the alkyl groups, cycloalkyl groups, aryl groups, aralkyl groups, alkyloxy groups, cycloalkyloxy groups, aryloxy groups and aralkyloxy groups, and the halogen atoms, silyl groups, heterocyclic groups, substituted amino groups and optionally protected hydroxyl groups, and the like, which are all mentioned in the definition of $R^1$, $R^2$, $R^3$ and $R^4$ in the above-mentioned general formula (2).

A further preferable tridentate aminodiphosphine ligand includes the following one.

[Chemical Formula 9]

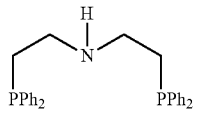

wherein, in the formula, Ph represents a phenyl group.

The tridentate aminodiphosphine ligands represented by the general formulas (2) and (10), which may form optically active ligands depending on the substituents on $Q^1$ and $Q^2$ or the species of $R^1$ to $R^8$, can be used as ligands for the ruthenium carbonyl complex represented by the general formula (1).

The ruthenium compound as a starting raw material for producing the ruthenium carbonyl complex in the present invention is not especially limited, and inorganic ruthenium compounds such as $RuCl_3$ hydrate, $RuBr_3$ hydrate and $RuI_3$ hydrate, $RuCl_2$ $(DMSO)_4$, $[Ru(cod)Cl_2]n$, $[Ru(nbd)Cl_2]n$, $(cod)Ru(2\text{-methallyl})_2$, $[Ru(benzene)Cl_2]_2$, $[Ru(benzene)Br_2]_2$, $[Ru(benzene)I_2]_2$, $[Ru(p\text{-cymene})Cl_2]_2$, $[Ru(p\text{-cymene})Br_2]_2$, $[Ru(p\text{-cymene})I_2]_2$, $[Ru(mesitylene)Cl_2]_2$, $[Ru(mesitylene)Br_2]_2$, $[Ru(mesitylene)I_2]_2$, $[Ru(hexamethylbenzene)Cl_2]_2$, $[Ru(hexamethylbenzene)Br_2]_2$, $[Ru(hexamethylbenzene)I_2]_2$, $RuCl_2$ $(PPh_3)_3$, $RuBr_2$ $(PPh_3)_3$, $RuI_2$ $(PPh_3)_3$, $RuH_4$ $(PPh_3)_3$, $RuClH(PPh_3)_3$, $RuH$ $(OAc)$ $(PPh_3)_3$, $RuH_2(PPh_3)_4$, and the like are exemplified.

In the list, DMSO represents dimethylsulfoxide, cod represents 1,5-cyclooctadiene, nbd represents norbornadiene, and Ph represents a phenyl group, respectively.

The ruthenium carbonyl complex represented by the general formula (1) can be easily produced from a tridentate aminodiphosphine ligand and a ruthenium carbonyl complex as a precursor.

The tridentate aminodiphosphine ligand can be easily produced by reacting a bis(substituted alkyl)amine having a leaving group and an alkali metal phosphide compound, wherein the alkali metal is lithium, sodium, potassium or the like.

The ruthenium carbonyl complex as a precursor can be obtained by the method described in Inorg. Synth, 1974, 15, 45 or the like. The obtained ruthenium carbonyl complex as a precursor is reacted with the tridentate aminodiphosphine ligand, and thereby the ruthenium carbonyl complex having a tridentate aminodiphosphine ligand of the present invention can be formed.

For example, the ruthenium carbonyl complex represented by the general formula (1) can be produced by reacting the tridentate aminodiphosphine ligand L represented by the general formula (2) and $RuXY(CO)$ $(P(Ar^5)_3)_3$ (wherein, in the formula, $Ar^5$s may be the same or different from one another, and each represents an optionally substituted aryl group. The aryl group and substituents in $Ar^5$ include the groups mentioned above. Preferable $Ar^5$s include phenyl groups which may be substituted with alkyl group(s), and the like. Especially, a phenyl group is exemplified.

A ruthenium carbonyl complex wherein X is $BH_4^-$ in the ruthenium carbonyl complex represented by the general formula (1) can be produced by reacting the ruthenium carbonyl complex wherein X is a chloride ion with a hydrogenated boron compound such as $NaBH_4$.

The complex produced in this way may generate steric isomers depending on the manner of coordination and conformation of the ligand. The complex used in the reaction may be either a mixture of said steric isomers or a pure single isomer.

A ruthenium carbonyl hydride-borohydride complex having a tridentate aminodiphosphine ligand, wherein $X=H^-$ (hydride) and $Y=BH_4^-$, can be obtained according to the method described in J. Am. Chem. Soc. 2005, 127, 516, or the like. These complexes are present being relatively stable, and are easily handled.

A preferable complex includes, for example, a complex represented by the following general formula (11)

RuHCl(CO)(L)                                    (11)

wherein in the formula, (L) means a tridentate aminodiphosphine ligand represented by the above-mentioned general formulas (2), (3) and (10), and the like. Said complex can be easily produced by stirring the tridentate aminodiphosphine ligand L represented by the general formula (2), (3) or (10) and $RuClH(CO)(PPh_3)_3$ in a suitable solvent.

As an another preferable complex includes, for example, a complex represented by the following general formula (12):

$RuH(BH_4)(CO)(L)$                              (12)

wherein in the formula, (L) means a tridentate aminodiphosphine ligand represented by the above-mentioned general formulas (2), (3) and (10), and the like. Said complex can be easily produced by stirring the ruthenium carbonyl complex represented by the general formula (11) and a boron hydrate compound such as NaBH$_4$ in a suitable solvent.

The amines as the raw materials in the present invention include primary and secondary amine compounds. These amines may be substituted with any substituents that do not adversely affect the alkylation method of the present invention. In the case where the amines as raw materials have a substituent that adversely affects the reaction, the substituent can be protected with a protective group in advance as necessary.

Accordingly, the method of the present invention can provide various aspects, but the elemental aspect of the method of the present invention is such a reaction that a primary or secondary amine compound generates a corresponding N-alkylated amine. Meanwhile, the term "alkylation" used in the present specification is not limited to a reaction for introducing an alkyl group, but is used as a convenient collective term for reactions for introducing a new C—N bond. Therefore, "alkylation" used in the present specification encompasses all reactions that for introducing new C—N into amines such as alkenylation, cycloalkylation, arylation and heteroarylation. Furthermore, "alkylation" in this specification encompasses both monoalkylation and dialkylation.

A preferable amine compound in the present invention includes an amine compound represented by the general formula (5).

$$R^4\text{—}NH_2 \quad (5)$$

R$^4$ in the general formula (5) represents an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s).

The alkyl group, cycloalkyl group, aryl group, aralkyl group, heterocyclic group, alkyloxy group, cycloalkyloxy group, aryloxy group and aralkyloxy group in R$^4$ in the general formula (5) include the groups that are mentioned in the definition of R$^1$, R$^2$, R$^3$ and R$^4$ in the above-mentioned general formula (2).

As the alkenyl group, a linear or branched alkenyl group including one or more carbon-carbon double bond(s) in the carbon chain and having 2 to 20 carbon atoms, preferably 2 to 15 carbon atoms, more preferably 2 to 10 carbon atoms is exemplified. Examples of such alkenyl group include a vinyl group, a 1-methyl-vinyl group, a 2-methyl-vinyl group, an n-2-propenyl group, a 1,2-dimethyl-vinyl group, a 1-methyl-propenyl group, a 2-methyl-propenyl group, n-1-butenyl group, an n-2-butenyl group, an n-3-butenyl group, and the like.

As the alkynyl group, a linear or branched alkynyl group including one or more carbon-carbon triple bond(s) in the carbon chain and having 2 to 10 carbon atoms, preferably 2 to 8 carbon atoms, more preferably 2 to 6 carbon atoms is exemplified. Examples of such alkynyl group include an ethynyl group, an n-1-propinyl group, an n-2-propinyl group, an n-1-butynyl group, an n-2-butynyl group, an n-3-butynyl group, and the like.

As the cycloalkenyl group, an unsaturated monocyclic, polycyclic or condensed cyclic cycloalkenyl group having 3 to 15 carbon atoms, preferably 3 to 10 carbon atoms is exemplified. Examples of such cycloalkenyl group include a cyclopropenyl group, a cyclopentenyl group, a cyclohexenyl group, a cyclooctenyl group, and the like.

The alkoxycarbonyl group includes a group constituted of linear or branched alkyl group having 1 to 20 carbon atoms, preferably 1 to 10 carbon atoms, and an oxycarbonyl group (—O—CO— group) bonded together. Examples of said alkoxycarbonyl group having 2 to 21 total carbon atoms, preferably 2 to 11 total carbon atoms include a methoxycarbonyl group, an ethoxycarbonyl group, an n-propoxycarbonyl group, an isopropoxycarbonyl group, and the like.

The cycloalkyloxycarbonyl group includes a group constituted of a monocyclic, polycyclic or condensed cyclic cycloalkyl group having 3 to 30 carbon atoms, preferably 3 to 20 carbon atoms, more preferably 3 to 10 carbon atoms, and an oxycarbonyl group (—O—CO— group) bonded together. Examples of said cycloalkyloxycarbonyl group having 4 to 31 total carbon atoms, preferably 4 to 21 total carbon atoms, more preferably 4 to 11 total carbon atoms include a cyclopropyloxycarbonyl group, a cyclopentyloxycarbonyl group, a cyclohexyloxycarbonyl group, a cyclooctyloxycarbonyl group, a bicyclo[1.1.0]butyloxycarbonyl group, a tricyclo[2.2.1.0]heptyloxycarbonyl group, a bicyclo[3.2.1]octyloxycarbonyl group, a bicyclo[2.2.2]octyloxycarbonyl group, an adamantyloxycarbonyl group (tricyclo[3.3.1.1]decanyloxycarbonyl group), a bicyclo[4.3.2]undecanyloxycarbonyl group, a tricyclo[5.3.1.1]dodecanyloxycarbonyl group, and the like.

The aryloxycarbonyl group includes a group constituted of a monocyclic, polycyclic or condensed cyclic aryl group having 6 to 36 carbon atoms, preferably 6 to 18 carbon atoms, more preferably 6 to 14 carbon atoms, and an oxycarbonyl group (—O—CO— group) bonded together. Examples of said aryloxycarbonyl group having 7 to 37 carbon atoms, preferably 7 to 19 carbon atoms, more preferably 7 to 15 carbon atoms include a phenyloxycarbonyl group, a naphthyloxycarbonyl group, an anthryloxycarbonyl group, a phenanthryloxycarbonyl group, a biphenyloxycarbonyl group, and the like.

The aralkyloxycarbonyl group includes a group constituted of an aralkyl group in which at least one hydrogen atom(s) in linear or branched alkyl group having 1 to 20 carbon atoms, preferably 1 to 10 carbon atoms has/have been substituted with the above-mentioned aryl group, preferably an aralkyl group having 7 to 15 carbon atoms, and an oxycarbonyl group (—O—CO— group) bonded together. Examples of said aralkyloxycarbonyl group include a benzyloxycarbonyl group, a 1-phenylethoxycarbonyl group, a 2-phenylethoxycarbonyl group, a 1-phenylpropoxycarbonyl group, a 3-naphthylpropoxycarbonyl group, and the like.

The alkenyloxycarbonyl group includes a group constituted of a linear or branched alkenyl group having 2 to 20 carbon atoms, preferably 2 to 15 carbon atoms, more preferably 2 to 10 carbon atoms, and an oxycarbonyl group (—O—CO— group) bonded together. Examples of said alkenyloxycarbonyl group having 3 to 21 total carbon atoms, preferably 3 to 16 total carbon atoms, more preferably 3 to 11 total carbon atoms include a vinyl group oxycarbonyl, a 1-methyl-vinyloxycarbonyl group, a 2-methyl-vinyloxycarbonyl group, an n-2-propenyloxycarbonyl group, a 1,2-dimethyl-vinyloxycarbonyl group, a 1-methyl-propenyloxycarbonyl group, a 2-methyl-propenyloxycarbonyl group, an n-1-butenyloxycarbonyl group, an n-2-butenyloxycarbonyl group, an n-3-butenyloxycarbonyl group, and the like.

The alkynyloxycarbonyl group includes a group constituted of a linear or branched alkynyl group including one or more carbon-carbon triple bond(s) in the carbon chain and having 2 to 10 carbon atoms, preferably 2 to 8 carbon atoms, more preferably 2 to 6 carbon atoms, and an oxycarbonyl group (—O—CO— group) bonded together. Examples of said alkynyloxycarbonyl group having 3 to 11 total carbon atoms, preferably 3 to 9 total carbon atoms, more preferably 3 to 7 total carbon atoms include an n-2-propinyloxycarbonyl group, an n-2-butynyloxycarbonyl group, an n-3-butynyloxycarbonyl group, and the like.

The cycloalkenyloxycarbonyl group includes a group constituted of an unsaturated monocyclic, polycyclic or condensed cyclic cycloalkenyl group having 3 to 15 carbon atoms, preferably 3 to 10 carbon atoms, and an oxycarbonyl group (—O—CO— group) bonded together. Examples of said cycloalkenyloxycarbonyl group having 4 to 16 total carbon atoms, preferably 4 to 11 total carbon atoms include a cyclopropenyloxycarbonyl group, a cyclopentenyloxycarbonyl group, a cyclohexenyloxycarbonyl group, a cyclooctenyloxycarbonyl group, and the like.

As the carboxamide group, a —CONH$_2$ group and a carboxamide group in which the nitrogen atom of the amide group is optionally substituted with the above-mentioned alkyl group(s) are exemplified.

The alkoxysulfonyl group includes a group constituted of a linear or branched alkyl group having 1 to 20 carbon atoms, preferably 1 to 10 carbon atoms, and an oxysulfonyl group (—O—SO$_2$— group) bonded together. Examples of said alkoxysulfonyl group include a methoxysulfonyl group, an ethoxysulfonyl group, an n-propoxysulfonyl group, an isopropoxysulfonyl group, and the like.

Said groups in $R^4$ may have substituent(s). Such "substituents" are not especially limited as long as they are groups that are not significant in the reaction in the present invention. Furthermore, in the case where it is possible that the substituents such as a hydroxyl group affect the reaction in the present invention, the substituents can also be protected by suitable protective groups prior to the reaction. Examples of "substituents" include halogen atoms, a hydroxyl group, a nitro group, a cyano group, a substituted or unsubstituted amino group, an alkylsilyl group, an alkyl group having 1 to 10 carbon atoms, an alkenyl group having 2 to 10 carbon atoms, a cycloalkyl group having 3 to 10 carbon atoms, an aryl group having 6 to 30 carbon atoms, an arylalkyl group having 7 to 30 carbon atoms, a heteroaryl group, an alkoxy group having 1 to 10 carbon atoms, an aryloxy group having 6 to 30 carbon atoms, an arylalkyloxy group having 7 to 30 carbon atoms, a heteroaryloxy group, and the like.

An another preferable amine compound of the present invention includes an amine compound represented by the general formula (8). The respective groups in $R^{B1}$ and $R^{B2}$ in the general formula (8) include the groups that are defined as $R^4$ in the above-mentioned general formula (5). $R^{B1}$ and $R^{B2}$ in the general formula (8) may bind to each other to form a ring together with the adjacent nitrogen atom. The thus-formed ring becomes a heterocycle containing at least one nitrogen atom. Preferable bound groups in the case where the ring is formed include linear or branched divalent alkylene group having 2 to 20 carbon atoms, preferably 4 to 10 carbon atoms, more preferably 4 to 6 carbon atoms; and linear or branched divalent alkenylene group having 4 to 20 carbon atoms, preferably 4 to 10 carbon atoms, more preferably 4 to 6 carbon atoms. Said divalent groups may have substituent(s) as those mentioned in the definition of $R^1$, $R^2$, $R^3$ and $R^4$. The alkylene chains or alkynylene chains may contain one or two or more phenylene group(s). Furthermore, the alkylene chains or alkynylene chains may contain one or two or more of heteroatom(s) selected from the group consisting of an oxygen atom, a nitrogen atom and a sulfur atom.

Examples of the amine in the ring structure include pyrrolidine, piperidine, piperazine, morpholine, and derivatives thereof, and the like.

The amine in the ring structure is referred to as "alicyclic amine" in this specification.

The amine wherein $R^A$ in the above-mentioned general formula (5) is an aryl group, and the amine wherein either or both of $R^{B1}$ or $R^{B2}$ in the general formula (8) is/are aryl group(s) are referred to as "arylamines" in this specification.

The amine wherein $R^A$ in the above-mentioned general formula (5) is a heterocyclic group, and the amine wherein either or both of $R^{B1}$ or $R^{B2}$ in the general formula (8) is/are heterocyclic group(s) are referred to as "heteroarylamines" in this specification.

The amine wherein $R^A$ in the above-mentioned general formula (5) is a cycloalkyl group, and the amine wherein either or both of $R^{B1}$ or $R^{B2}$ in the general formula (8) is/are cycloalkyl group(s) are referred to as "cycloalkylamines" in this specification. Furthermore, in the case where the cycloalkyl group(s) is/are bridged cycloalkyl group(s) such as bicyclo group(s) and tricyclo group(s), these amines are referred to as "bridged cycloalkylamines".

The alcohols as the raw material compound in the method of the present invention include compounds having one or more, preferably from 1 to 5, more preferably from 1 to 3 primary or secondary alcoholic hydroxyl group(s). In the raw material compound, an amino group, a hydroxyl group, and the like may be present besides the primary or secondary alcoholic hydroxyl group(s).

A preferable example of the alcohols that become the raw material compound in the method of the present invention includes an alcohol represented by the general formula (6).

The aryl groups and heterocyclic groups represented by R in the general formula (6) include the groups that are mentioned in the definition of $R^1$, $R^2$, $R^3$ and $R^4$ in the above-mentioned general formula (2).

The hydrocarbon groups represented by R in the general formula (6) include a linear or branched alkyl group having 1 to 20 carbon atoms, preferably 1 to 15 carbon atoms, more preferably 1 to 10 carbon atoms; linear or branched alkenyl group having 2 to 20 carbon atoms, preferably 2 to 15 carbon atoms, more preferably 2 to 10 carbon atoms; a linear or branched alkynyl group having 2 to 10 carbon atoms, preferably 2 to 8 carbon atoms, more preferably 2 to 6 carbon atoms; a saturated or unsaturated monocyclic, polycyclic or condensed cyclic alicyclic hydrocarbon group having 3 to 15 carbon atoms, preferably 3 to 10 carbon atoms; a monocyclic, polycyclic, or condensed cyclic aryl group having 6 to 36 carbon atoms, preferably 6 to 18 carbon atoms, or 6 to 12 carbon atoms; an aralkyl group having 7 to 40 carbon atoms, preferably 7 to 20 carbon atoms, or 7 to 15 carbon atoms; and the like. These groups may have "substituents", and said substituents are not especially limited as long as they are groups that are not significant in the reaction of the present invention. Furthermore, in the case where it is possible that the substituents such as a hydroxyl group affect the reaction in the present invention, the substituents can also be protected by suitable protective groups prior to the reaction. Examples of "substituents" include halogen atoms, a hydroxyl group, a nitro group, a cyano group, a substituted or unsubstituted amino group, an alkylsilyl groups, an alkyl group having 1 to 10 carbon atoms, an alkenyl group having 2 to 10 carbon atoms, a cycloalkyl group having 3 to 10 carbon atoms, an aryl group having 6 to 30 carbon atoms, an arylalkyl group having 7 to 30 carbon atoms, a heteroaryl groups, an alkoxy group having 1 to 10 carbon atoms, an aryloxy group having 6 to 30 carbon atoms, an arylalkyloxy group having 7 to 30 carbon atoms, a heteroaryloxy groups, and the like.

Especially preferable examples of R in the general formula (6) include a linear or branched alkyl group having 1 to 20 carbon atoms, preferably 1 to 15 carbon atoms, more preferably 1 to 10 carbon atoms; an aralkyl group having 7 to 40 carbon atoms, preferably 7 to 20 carbon atoms, or 7 to 15 carbon atoms; and the like. Said alkyl groups and aralkyl groups may be substituted with the above-mentioned "substituents".

The method for alkylating amines of the present invention can be preferably conducted in the alcohol that is used as the reaction agent, or in other solvent. As the solvent to be used, solvent that can dissolve substrates and catalysts is preferable, and a single solvent or a mixed solvent can be used. Specifically, aromatic hydrocarbons such as toluene and xylene, aliphatic hydrocarbons such as hexane and heptane, halogenated hydrocarbons such as methylene chloride and chlorobenzene, ethers such as diethyl ether, tetrahydrofuran, methyl tert-butyl ether and cyclopentylmethyl ether, alcohols such as methanol, ethanol, isopropyl alcohol, n-butyl alcohol, 2-butanol and tert-butyl alcohol, and polyvalent alcohols such as ethylene glycol, propylene glycol, 1,2-propanediol and glycerin are included. Among these, ethers or alcohols are preferable, and tetrahydrofuran, methanol or isopropanol is included in an especially preferable solvent. The use amount of the solvent can be suitably selected depending on reaction conditions and the like. The reaction is conducted under stirring as necessary.

The use amount of the catalyst differs depending on the alcohols as a substrate, the reaction conditions, the species of the catalyst, and the like, and is generally within a range of from 0.0001 mol % to 10 mol %, preferably within a range of from 0.005 mol % to 5 mol % on the basis of the molar ratio of the ruthenium metal to the substrate amines. In the method of the present invention, the reaction temperature in conducting the alkylation reaction is from 50° C. to 200° C., preferably from 80° C. to 180° C. If the reaction temperature is too low, it is not preferable since much unreacted raw materials may remain.

Hydrogen is not required in conducting the method of the present invention. Where necessary, compression or decompression can also be conducted during the reaction in the method of the present invention. In the case where compression is conducted, nitrogen or hydrogen gas may be used. Furthermore, compression can be conducted by the vapor pressure of the solvent.

The reaction time in the method of the present invention is from 30 minutes to 72 hours, preferably from 2 hours to 48 hours, and a sufficiently high raw material conversion rate can be achieved within the reaction time.

After the reaction is completed, the intended alkylated amines can be obtained by using generally-used purification processes such as extraction, filtration, crystallization, distillation and various types of chromatography, either singly or in a suitable combination.

In other words, the method for alkylating amines of the present invention includes the following processes of (1) and (2).

(1) A process of reacting an amine with an alcohol in the presence of a ruthenium complex represented by the above-mentioned general formula (1), and (2) a process of obtaining an N-alkylamine generated in the above-mentioned reaction.

It is not especially necessary to add additive(s) to the reaction of the amine and alcohol in the method of the present invention, but suitable additive(s) may be added as necessary, and the method may further include a process of adding such additive(s) to the reaction system. Examples of such additive include basic substances. As the basic substances, alkali metal carbonates such as potassium carbonate, sodium carbonate, lithium carbonate and cesium carbonate, alkaline earth metal carbonates such as magnesium carbonate and calcium carbonate, alkali metal hydrogencarbonates such as sodium hydrogencarbonate and potassium hydrogencarbonate, alkali metal hydroxides such as sodium hydroxide, potassium hydroxide and lithium hydroxide, alkaline earth metal hydroxides such as magnesium hydroxide and calcium hydroxide, alkali metal alkoxides such as sodium methoxide, sodium ethoxide, sodium isopropoxide, sodium tert-butoxide, potassium methoxide, potassium ethoxide, potassium isopropoxide, potassium tert-butoxide, lithium methoxide, lithium isopropoxide and lithium tert-butoxide, alkaline earth metal alkoxides such as magnesium methoxide and magnesium ethoxide, and metal hydrides such as sodium hydride and calcium hydride are exemplified. Especially preferable basic substances include strong basic substances such as sodium methoxide or potassium tert-butoxide, and the like. Such basic substance, preferably a strong basic substance is added in an equivalent amount of from 0.01 to 1, preferably from 0.1 to 0.8 per amines. By adding such basic substance, a high conversion rate can be achieved.

EXAMPLES

Hereinafter, the present invention will be described in detail with reference to Examples, but it is not intended that the present invention is limited thereto.

In the Examples, the following analyzing devices were employed.

Nuclear magnetic resonance spectrometer (NMR); MERCURY300-C/H (VARIAN)

Gas chromatography (GC); GC-4000 (GL Sciences, Inc.)

Column; Inert Cap 1 (GL Sciences, Inc.)

HRMS; LCMS-IT-TOF (Shimadzu Corp.)

(Reference Example 1) Production of Ruthenium Carbonyl Complex 1

1.4 g of ruthenium carbonyl complex 1 was produced according to the method described in WO 2011/048727 A1.

[Chemical Formula 10]

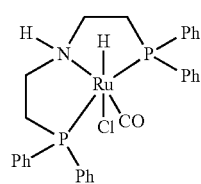

1

(Reference Example 2) Production of Ruthenium Carbonyl Complex 2

Ruthenium carbonyl complex 2 was produced according to the method described in WO 2011/048727 A1, wherein the reaction was carried out according to the following reaction formula.

[Chemical Formula 11]

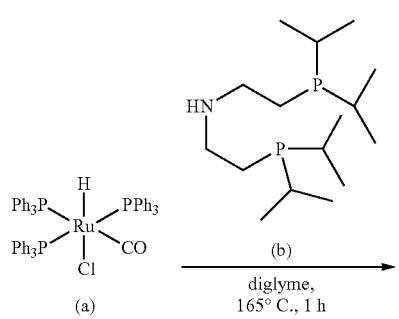

2

[Chemical Formula 12]

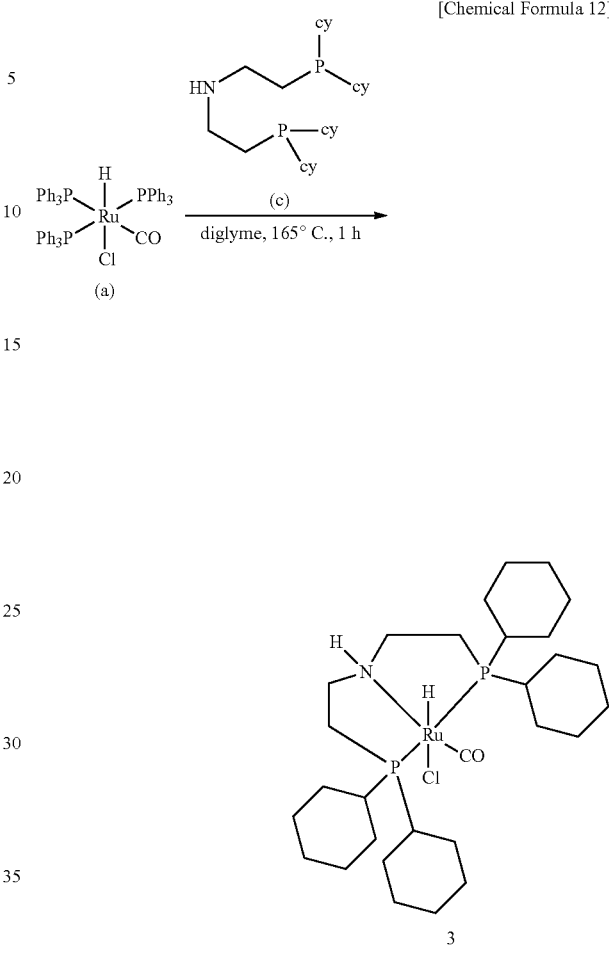

3

Under a nitrogen atmosphere, 329 mg (1.07 mmol) of ligand (b) and 922 mg (0.956 mmol) of ruthenium complex (a) as a raw material were added to a 20 ml Schlenk tube, 3 ml of diglyme was added, and the mixture was heated at 165° C. for 1 hour. The reaction mixture was cooled to −15° C., the precipitated crystals were separated by filtration, and the crystals were washed with diethyl ether. The obtained crystals were dried in vacuo, whereby 180 mg (0.39 mmol) of ruthenium carbonyl complex 2 was obtained.

$^1$H-NMR (300 MHz CD$_2$Cl$_2$): δ=−16.30 (t, J=18.0 Hz, 1H), 1.01-1.49 (m, 24H), 1.72-1.84 (m, 4H), 2.20-2.36 (m, 4H), 2.62-2.70 (m, 2H), 3.15-3.33 (m, 2H), 3.42 (bs, 1H)

$^{31}$P-NMR (121.5 MHz CD$_2$Cl$_2$): δ=75.1 (s)

HRMS(ESI): m/z

As C$_{17}$H$_{38}$NOP$_2$ClRu, calculated value: [M]$^+$ 471.1155; measured value: 471.1133.

(Reference Example 3) Production of Ruthenium Carbonyl Complex 3

Ruthenium carbonyl complex 3 was produced according to the method described in WO 2011/048727 A1, wherein the reaction was carried out according to the following reaction formula.

Under a nitrogen atmosphere, 706 mg (1.52 mmol) of ligand (c) and 1320 mg (1.37 mmol) of ruthenium complex (a) as a raw material were added to a 20 ml Schlenk tube, 4.3 ml of diglyme was added, and the mixture was heated at 165° C. for 1 hour. The reaction mixture was cooled to 0° C., the precipitated crystals were separated by filtration, and the crystals were washed with diethyl ether. The obtained crystals were dried in vacuo, whereby 581 mg (0.92 mmol) of ruthenium carbonyl complex 3 was obtained.

$^1$H-NMR (300 MHz CD$_2$Cl$_2$): δ=−16.37 (t, J=18.0 Hz, 1H), 1.25-2.02 (m, 50H), 2.20-2.40 (m, 8H), 3.19-3.25 (m, 2H), 3.50-3.52 (m, 2H)

$^{31}$P-NMR (121.5 MHz CD$_2$Cl$_2$): δ=52.8 (d, J=14 Hz)

HRMS(ESI): m/z

As C$_{29}$H$_{54}$NOP$_2$ClRu, calculated value: [M]$^+$ 631.2407; measured value: 631.2427.

(Reference Example 4) Production of Ruthenium Carbonyl Complex 4

Ruthenium carbonyl complex 4 was produced according to the method described in WO 2011/048727 A1, wherein the reaction was carried out according to the following reaction formula.

[Chemical Formula 13]

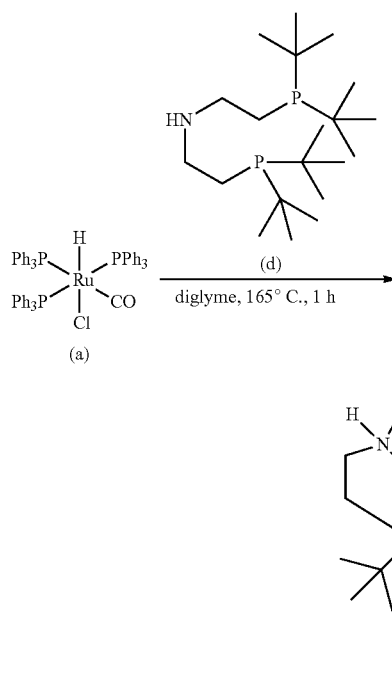

Under a nitrogen atmosphere, 494 mg (1.29 mmol) of ligand (d) and 1120 mg (1.16 mmol) of ruthenium complex (a) as a raw material were added to a 20 ml Schlenk tube, 3.6 ml of diglyme was added, and the mixture was heated at 165° C. for 1 hour. The reaction mixture was cooled to 0° C., the precipitated crystals were separated by filtration, and the crystals were washed with diethyl ether. The obtained crystals were dried in vacuo, whereby 350 mg (0.92 mmol) of ruthenium carbonyl complex 4 was obtained.

$^1$H-NMR (300 MHz $CD_2Cl_2$): δ=−18.76 (t, J=19.8 Hz, 1H), 1.32 (s, 9H), 1.34 (s, 9H), 1.42 (s, 9H), 1.44 (s, 9H), 2.04-2.28 (m, 4H), 2.37-2.47 (m, 2H), 3.11-3.58 (m, 3H)

$^{31}$P-NMR (121.5 MHz $CD_2Cl_2$): δ=86.7 (d, J=15 Hz)

HRMS(ESI): m/z

As $C_{21}H_{46}NOP_2Ru$, calculated value: [M-Cl]$^+$ 492.2099; measured value: 492.2093.

Examples 1 to 5

Monomethylation Reaction of Primary Amine with Methanol

[Chemical Formula 14]

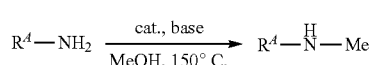
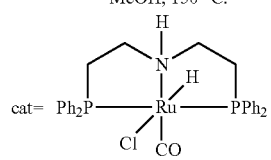

1.2 mg (0.002 mmol) of complex 1, which was produced in Reference Example 1, was added to a 100 ml stainless autoclave, nitrogen substitution was conducted, and 2 ml of methanol was then added thereto. An amine (2 mmol) and a 1 M methanol solution of NaOMe as a base were then added, and the mixture was stirred at 150° C. for 5 hours. After cooling, the reactant was analyzed by GC, and the result of the analysis is shown in the following Table 1.

TABLE 1

| Example | Substrate | Base (per amine equivalent amount) | GC yield (%) |
|---|---|---|---|
| 1 | Aniline | 0.6 | 100 |
| 2 | 4-Fluoroaniline | 0.2 | 84 |
| 3 | 4-Chloroaniline | 0.6 | 100 |
| 4 | p-Toluidine | 0.6 | 100 |
| 5 | 2-Aminopyridine | 0.6 | 76 |

(Example 6) Monomethylation Reaction of Aniline with Methanol 4.7 mg (0.01 mmol) of complex 2, which was produced in Reference Example 2, was added to a 100 ml stainless autoclave, nitrogen substitution was conducted, and 2 ml of methanol was then added thereto. 0.183 ml (2 mmol) of aniline and 1.2 ml (1.2 mmol) of a 1 M methanol solution of NaOMe were then added, and the mixture was then stirred at 170° C. for 5 hours. After cooling, the reactant was analyzed by GC, and 1-methylaniline was obtained at a GC yield of 88%.

(Example 7) Monomethylation Reaction of Aniline with Methanol 6.3 mg (0.01 mmol) of complex 3, which was produced in Reference Example 3, was added to a 100 ml stainless autoclave, nitrogen substitution was conducted, and 2 ml of methanol was then added thereto. 0.183 ml (2 mmol) of aniline and 1.2 ml (1.2 mmol) of a 1 M methanol solution of NaOMe were then added, and the mixture was then stirred at 170° C. for 5 hours. After cooling, the reactant was analyzed by GC, and 1-methylaniline was obtained at a GC yield of 62%.

(Example 8) Monoethylation Reaction of Aniline with Ethanol

[Chemical Formula 15]

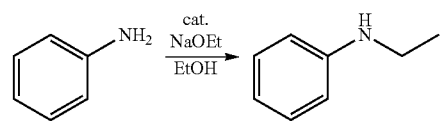

1.2 mg (0.002 mmol) of complex 1, which was produced in Reference Example 1, was added to a 100 ml stainless autoclave, nitrogen substitution was conducted, and 2 ml of ethanol was then added thereto. 0.183 ml (2 mmol) of aniline and 0.45 ml (1.2 mmol) of a 2.68 M ethanol solution of NaOEt were then added, and the mixture was then stirred at 150° C. for 5 hours. After cooling, the reactant was analyzed by GC, and 1-ethylaniline was obtained at a GC yield of 65%.

(Example 9) Monobenzylation Reaction of Aniline with Benzyl Alcohol

[Chemical Formula 16]

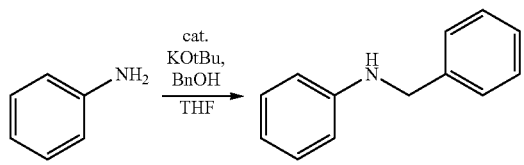

1.2 mg (0.002 mmol) of complex 1, which was produced in Reference Example 1, and 44.9 mg (0.4 mmol) of KOtBu were added to a 100 ml stainless autoclave, nitrogen substitution was conducted, and 2.9 ml of tetrahydrofuran (THF) was then added thereto. 0.183 ml (2 mmol) of aniline and 0.31 ml (3 mmol) of benzyl alcohol (BnOH) were then added, and the mixture was then stirred at 150° C. for 5 hours. After cooling, the reactant was analyzed by GC, and 1-benzylaniline was obtained at a GC yield of 73%.

(Example 10) Methylation Reaction of Piperidine with Methanol

[Chemical Formula 17]

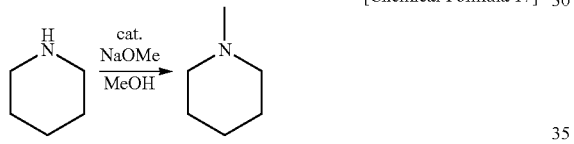

1.2 mg (0.002 mmol) of complex 1, which was produced in Reference Example 1, was added to a 100 ml stainless autoclave, nitrogen substitution was conducted, and 2 ml of methanol was then added thereto. 0.198 ml (2 mmol) of piperidine and 0.4 ml (0.4 mmol) of a 1 M methanol solution of NaOMe were then added, and the mixture was then stirred at 150° C. for 5 hours. After cooling, the reactant was analyzed by GC, and N-methylpiperidine was obtained at a GC yield of 58%.

(Example 11) Methylation Reaction of 1-Adamantylamine with Methanol

[Chemical Formula 18]

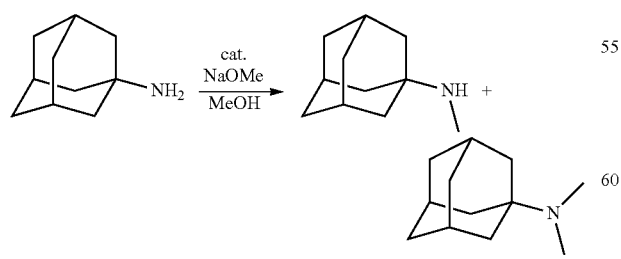

6.0 mg (0.01 mmol) of complex 1 produced in Reference Example 1 and 303 mg (2 mmol) of 1-adamantylamine were added to a 100 ml stainless autoclave, nitrogen substitution was conducted, and 2 ml of methanol was then added thereto. Next, 1.1 ml (1.2 mmol) of 1.13 M methanol solution of NaOMe was added, and the mixture was then stirred at 150° C. for 5 hours. After cooling, the reactant was analyzed by GC, and N-methyladamantylamine was obtained at a GC yield of 19% and N,N-dimethyladamantylamine was obtained at a GC yield of 37%.

INDUSTRIAL APPLICABILITY

The present invention provides a convenient, safe and efficient method for alkylating amines by directly using alcohols themselves as alkylating agents, and this method is an industrial method for alkylating amines using alcohols, which are highly safer and more eco-friendly raw materials as compared to conventional alkylating agents, and is also a useful method in chemical industries such as pharmaceutical industry, agrochemical industry and food industry.

The invention claimed is:

1. A method for producing an N-alkylamine, comprising reacting an amine with an alcohol in the presence of a ruthenium complex represented by the following general formula (1):

$$\text{RuHCl(CO)(L)} \quad (1)$$

wherein, the general formula (1), L represents a tridentate aminodiphosphine ligand represented by the following general formula (2):

(2)

wherein, in the general formula (2),
$R^1$, $R^2$, $R^3$ and $R^4$ may be the same or different from one another, and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group or a substituted amino group, wherein $R^1$ and $R^2$ or $R^3$ and $R^4$ may bind to each other to form a ring together with the adjacent phosphorus atom, and said alkyl group, cycloalkyl group, aryl group, aralkyl group, alkyloxy group, cycloalkyloxy group, aryloxy group, aralkyloxy group, heterocyclic group and substituted amino group may have substituent(s); and
$Q^1$ and $Q^2$ may be the same or different from each other, and each represents an optionally substituted divalent alkylene group, an optionally substituted divalent cycloalkylene group or an optionally substituted divalent aralkylene group,
wherein the N-alkylamine has the following general formula (4) or (9):

$$\text{R—NH—R}^A \quad (4)$$

or

(9)

wherein, in the general formula (4) or (9),

R represents an optionally substituted hydrocarbon group, an optionally substituted aryl group or an optionally substituted heterocyclic group, and $R^4$ represents an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s); and wherein the amine has the following general formula (5):

$$R^4\text{—}NH_2 \tag{5}$$

wherein, in the general formula (5), $R^4$ represents the same group as in the definition in the general formula (4) or (9), and the alcohol has the following general formula (6):

$$R\text{—}OH \tag{6}$$

wherein, in the general formula (6), R represents the same group as in the definition in the general formula (4) or (9).

2. The production method according to claim 1, wherein L is a tridentate aminodiphosphine ligand represented by the following general formula (3):

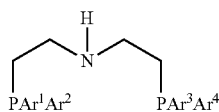

(3)

wherein, in the general formula (3), $Ar^1$, $Ar^2$, $Ar^3$ and $Ar^4$ may be the same or different from one another, and each represents an optionally substituted aryl group or an optionally substituted aromatic heterocyclic group.

3. The production method according to claim 1, wherein the N-alkylamine has the general formula (4):

wherein, in the general formula (4), $R^4$ represents an aryl group or an aromatic heterocyclic group, which groups may comprise substituent(s).

4. The production method according to claim 1, wherein the N-alkylamine has the general formula (9):

(9)

wherein, in the general formula (9), $R^4$ represents an aryl group, or an aromatic heterocyclic group which groups may comprise substituent(s).

5. The method according to claim 1, wherein the alcohol is a primary or secondary alcohol.

6. The method according to claim 1, wherein the alcohol is methanol or ethanol.

7. The method according to claim 1, wherein the reaction of the amine and the alcohol is conducted in the presence of a basic substance.

8. The method according to claim 7, wherein the basic substance is a metal alkoxide.

9. A method for producing an N-alkylamine, comprising reacting an amine with an alcohol in the presence of a ruthenium complex represented by the following general formula (1):

$$RuHCl(CO)(L) \tag{1}$$

wherein, the general formula (1), L represents a tridentate aminodiphosphine ligand represented by the following general formula (2):

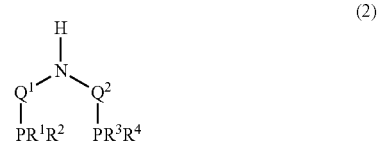

(2)

wherein, in the general formula (2), $R^1$, $R^2$, $R^3$ and $R^4$ may be the same or different from one another, and each represents a hydrogen atom, an alkyl group, a cycloalkyl group, an aryl group, an aralkyl group, an alkyloxy group, a cycloalkyloxy group, an aryloxy group, an aralkyloxy group, a heterocyclic group or a substituted amino group, wherein $R^1$ and $R^2$ or $R^3$ and $R^4$ may bind to each other to form a ring together with the adjacent phosphorus atom, and said alkyl group, cycloalkyl group, aryl group, aralkyl group, alkyloxy group, cycloalkyloxy group, aryloxy group, aralkyloxy group, heterocyclic group and substituted amino group may have substituent(s); and $Q^1$ and $Q^2$ may be the same or different from each other, and each represents an optionally substituted divalent alkylene group, an optionally substituted divalent cycloalkylene group or an optionally substituted divalent aralkylene group, wherein the N-alkylamine has the following general formula (7):

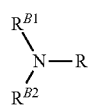

(7)

wherein, in the general formula (7), $R^{B1}$ represents a hydrogen atom, an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s);

$R^{B2}$ represents an alkyl group, a cycloalkyl group, an aryl group, an aralkyl group, a heterocyclic group, an alkenyl group, an alkynyl group, a cycloalkenyl group, an alkyloxy group, a cycloalkyloxy group, an aryloxy group, an aralkyloxy group, a hydroxyl group, an alkoxycarbonyl group, a cycloalkyloxycarbonyl group, an aryloxycarbonyl group, an aralkyloxycarbonyl group, an alkenyloxycarbonyl group, an alkynyloxycarbonyl group, a cycloalkenyloxycarbonyl group, a carboxamide group or an alkoxysulfonyl group, which groups may comprise substituent(s);

wherein $R^{B1}$ and $R^{B2}$ may bind to each other to form a ring together with the adjacent nitrogen atom; and R represents an optionally substituted hydrocarbon group, an optionally substituted aryl group or an optionally substituted heterocyclic group, wherein the amine has the following general formula (8):

  (8)

wherein, in the general formula (8), $R^{B1}$ and $R^{B2}$ each represents the same group as the definition in the general formula (7), and the alcohol has the following general formula (6):

  (6)

wherein, in the general formula (6), R represents the same group as mentioned above.

10. The production method according to claim 9, wherein L is a tridentate aminodiphosphine ligand represented by the following general formula (3):

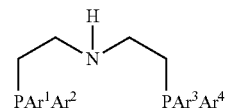  (3)

wherein, in the general formula (3), $Ar^1$, $Ar^2$, $Ar^3$ and $Ar^4$ may be the same or different from one another, and each represents an optionally substituted aryl group or an optionally substituted aromatic heterocyclic group.

11. The production method according to claim 9, wherein, in the general formula (7), $R^{B1}$ represents an aryl group or an aromatic heterocyclic group, which groups may comprise substituent(s).

12. The method according to claim 9, wherein the alcohol is a primary or secondary alcohol.

13. The method according to claim 9, wherein the alcohol is methanol or ethanol.

14. The method according to claim 9, wherein the reaction of the amine and the alcohol is conducted in the presence of a basic substance.

15. The method according to claim 14, wherein the basic substance is a metal alkoxide.

* * * * *